United States Patent [19]

Tresper et al.

[11] 4,048,200
[45] Sept. 13, 1977

[54] 1,1,2-TRIS-(o/p-HYDROXYPHENYL)-1-PHENYL-ETHANES

[75] Inventors: Erhard Tresper; Dieter Neuray; Dieter Freitag, all of Krefeld, Germany

[73] Assignee: Bayer Aktiengesellschaft, Germany

[21] Appl. No.: 660,850

[22] Filed: Feb. 24, 1976

[30] Foreign Application Priority Data

Feb. 28, 1975 Germany .............................. 2508710

[51] Int. Cl.² ............................................. C07C 39/16
[52] U.S. Cl. ................................................... 260/395
[58] Field of Search ........................... 260/395, 348 R

[56] References Cited

U.S. PATENT DOCUMENTS

| | | | |
|---|---|---|---|
| 3,057,928 | 10/1962 | Koblitz et al. | 260/395 X |
| 3,123,586 | 3/1964 | Rust et al. | 260/348 R X |
| 3,378,525 | 4/1968 | Sellers | 260/348 R X |
| 3,787,451 | 1/1974 | Mah | 260/348 R |
| 3,957,832 | 5/1976 | Bressler et al. | 260/395 X |

FOREIGN PATENT DOCUMENTS 1,184,289  3/1970  United Kingdom ................. 260/395

*Primary Examiner*—Allen B. Curtis
*Attorney, Agent, or Firm*—Connolly and Hutz

[57] ABSTRACT

New [1,1,2-tris-(o/p-hydroxyphenyl)-1-phenyl-ethanes] and their preparation by reacting acetophenone derivatives with phenol at temperatures between −20° and 200° C.

4 Claims, No Drawings

1,1,2-TRIS-(o/p-HYDROXYPHENYL)-1-PHENYL-ETHANES

This invention relates to new 1,1,2-tris-(o/p-hydroxyphenyl)-1-phenyl-ethanes.

It is known that 2,2-bis-(p-hydroxyphenyl)-propane (Bisphenol A) is produced on a large technical scale by the reaction of acetone with phenol. Almost quantitative yields are obtained (Ullmanns Enzyklopadie der Techn. Chemie, 1962, Volume 13, page 448; Kirk-Othmar, Encyclopedia of Chemical Technology, 1963, Volume 2, page 912). It is also known to react monochloroacetone with phenol to produce 1,2,2-tris-(p-hydroxyphenyl)-propane which is very difficult to purify. It cannot be crystallised and can only be isolated in a heavily coloured, so-called colloidal state (Ber.,.dtsch. Chem.Ges. 45, 2490 (1912)). Purification is therefore omitted when purity is not essential for subsequent reactions (U.S. Pat. No. 2,965,611).

It is also known that if a methyl group of acetone is replaced by a larger substituent, for example by a phenyl group, only quite low yields can be obtained even after very long reaction times; for example the reactions of acetophenone with phenol (Ann.507, 21 (1933), Ann.363, 275 (1908) and J. Am.Soc. 61, 345 (1939)) or of p-hydroxyacetophenone with phenol (German Offenlegungsschrift No. 1,930,333) are very slow and result in very unsatisfactory yields. If both methyl groups of acetone are replaced, for example with phenyl groups, virtually no reaction takes place with phenol.

It has now surprisingly been found that acetophenones which are substituted in the ω-position react readily with phenols to give rise to high yields of new tris-phenols which can be readily crystallised and easily purified.

The present invention therefore relates to trisphenols [1,1,2-tris-(o/p-hydroxyphenyl)-1-phenyl-ethanes] of the general formula (I):

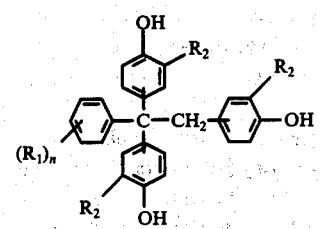

wherein:

$R_1$ and $R_2$, which may be the same or different, represent hydrogen, an alkyl group containing from 1 to 18 preferably from 1 to 4 C atoms, most preferably methyl a cyclohexyl group or an optionally substituted aryl group containing from 6 to 15 C atoms, preferably phenyl, or a halogen atom or a nitro group, and $n$ represents an integer of from 1 to 5, preferably from 1 to 3.

The invention also relates to a process for the preparation of the new trisphenols wherein ω-substituted acetophenones of the general formula (II)

(II)

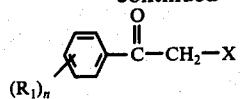

wherein:

X denotes a halogen atom, preferably chlorine or bromine, or a hydroxyl group, and $R_1$ and $n$ have the meanings indicated above, are reacted with an at least three times and preferably five to 15 times equivalent quantity of a phenol of the general formula (III)

(III)

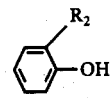

wherein:

$R_2$ has the meaning indicated above; at temperatures between −20° and 200° C, preferably between 15° and 120° C, optionally in the presence of an acid catalyst.

The following are examples of substituted ω-acetophenones which are suitable for the process according to the invention: ω-Chloroacetophenone, 4-fluoro-ω-chloroacetophenone, 4, ω-dichloroacetophenone, 3,4,ω-trichloroacetophenone, phenacyl alcohol, 4-chloro-ω-hydroxyacetophenone, ω-bromoacetophenone, 3,5-dichloro-ω-bromoacetophenone, ω-chloro-2,4,6-tribromoacetophenone, ω-chloro-2-nitroacetophenone, ω-chloro-3-nitroacetophenone, ω-chloro-4-nitroacetophenone, 4,ω-dichloro-3-nitroacetophenone, ω-bromo-4-methyl-acetophenone, 4,5-dichloro-ω-bromo-2-nitroacetophenone, ω-chloro-2-methylacetophenone and ω-chloro-4-methylacetophenone.

The compounds can be easily prepared from the corresponding acetophenones by conventional methods, for example phenacyl chlorides are obtained by slowly introducing the stoichiometric quantity of chlorine into a solution of the corresponding acetophenone in glacial acetic acid at temperatures between 0° and 15° C. When no discoloration due to chlorine can be seen in the reaction solution, the solvent is evaporated off in a water jet vacuum and the residue is purified by distillation or crystallisation.

Phenols which have the structure of the formula (III) already indicated above are suitable starting compounds for the process according to the invention are reactants for the above mentioned ω-substituted acetophenones. The following are examples:

Phenol, o-methylphenol, o-ethylphenol, o-isopropylphenol, o-tert.-butylphenol, o-fluorophenol, o-chlorophenol, o-bromophenol, o-cyclohexylphenol and o-phenylphenol.

In the process according to the invention, the reaction of the substituted acetophenones with phenols may be carried out in the presence of acid catalysts. Any acid may be used for this purpose, for example mineral acids such as hydrochloric acid, hydrobromic acid, sulphuric acid, phosphoric acid, polyphosphoric acids, boric acid or tetrafluoroboric acid; aromatic and aliphatic carboxylic acids, particularly halogenated carboxylic acids such as fluorinated or chlorinated acetic or propionic acids; aliphatic or aromatic sulphonic acids such as methanesulphonic acid, hexanesulphonic acid, dodecanesulphonic acid, cyclohexanesulphonic acid, benzenesulphonic acid, toluenesulphonic acid, parachlorobenzenesulphonic acid, benzene-1,3-disulphonic acid, naphthalenesulphonic acid and naphthalene disulphonic acids; and aliphatic and aromatic phosphonic acids and phosphinic acids such as cyclohexylphosphonic acid, phenylphosphonic acid and dimethylphosphinic acid.

Lewis acids may also be used, for example zinc-(II) chloride, tin-(II) chloride, boron trifluoride, aluminum chloride, iron chloride and titanium tetrachloride.

Acid activated silicas and Fuller's earths such as montmorrillonite, silicoaluminates and silica gel may also be used as acid catalysts. Silicas are finely divided materials which contain silicic acid and/or aluminium oxide. These silicas and Fuller's earths can be activated in known manner by acid treatment (Chemie fur Labor und Betrieb, 1956, page 422, Ullmann, 3rd Edition, Volume 9, page 271 et seq; Volume 8 pages 801 to 804). This activation may be carried out using mineral acids such as sulphuric acid, phosphoric acid, hydrochloric acid, perchloric acid or hydrofluoric acid.

Natural or synthetic acid ion exchangers such as zeolites or exchanger resins may also be used. By exchanger resins are meant insoluble resins consisting of inert, two-dimensionally or three-dimensionally cross-linked polymers which are substituted with reactive groups such as phosphoric, phosphonic, sulphuric or sulphonic acid groups.

In particular, it is suitable to use resins which contain one sulphonic acid group per 0.5 to 2 monomer units of the resin (Ullmann, 3rd Edition, Volume 8, pages 806 to 822, in particular page 816; German Patent Specification 915 267).

Acid activated molecular sieves may also be used. It is also possible to use mixtures of the above mentioned acids and/or acid activated silicas and Fuller's earths and/or acid ion exchangers.

The quantity of acid catalyst used may vary within wide limits although generally only catalytic quantities are required for carrying out the process according to the invention, particularly since acids are formed during the reaction of phenacyl chlorides and bromides. It has been found that when these compounds are used, an additional acid catalyst merely accelerates the onset of the reaction but is not essential since the reaction can frequently be started simply by mild heating. Optimal results are obtained using quantities of catalyst between 0.05 and 2 mol per mol of acetophenyl compound.

The reaction time is very variable. It may be vary between a few minutes and 24 hours, depending on whether the reaction is carried out batchwise in a reaction vessel or pressure vessel, or continuously, for example in a reaction tube. Suitable procedures and apparatus for carrying out the process according to the invention on a technical scale can be selected from those already known in the art.

The process may be carried out at temperatures of between −20° and 200° C, preferably between 15° and 120° C. It may be carried out at normal pressure, reduced pressure or excess pressure.

The process according to the invention may be carried out in suitable solvents and/or diluents.

Compounds which are inert under the reaction conditions may be used for this purpose, for example aromatic hydrocarbons which may be halogenated, preferably with bromine or chlorine or substituted with NO₂ groups, such as benzene, toluene, xylenes, chlorobenzene, dichlorobenzenes, nitrobenzene and aliphatic, optionally halogenated hydrocarbons such as n-hexane, carbon tetrachloride or 1,2-dicloroethane.

According to one particularly advantageous embodiment of the process according to the invention, the phenol used in excess constitutes the reaction medium so that no additional solvent and/or diluent is required.

According to one preferred embodiment of the process of the invention, the phenacyl compound, e.g. phenacyl chloride, is mixed with 15 times the molar quantity of the phenol, e.g. phenol itself, and hydrogen chloride is introduced at 60° C until the mixture is saturated with it. Stirring is then continued for a further 5 to 6 hours at 60° C and the hydrochloric acid formed in the reaction and excess phenol are distilled off in a water jet vacuum and the residue is digested with methylene chloride. The product can be recrystallised, for example from methanol/water. The process may be illustrated by the following reaction scheme for the preparation of 1,1,2-tris-(p-hydroxyphenyl)-1-phenyl-ethane:

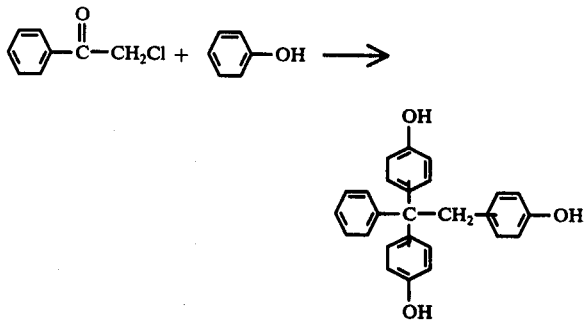

As already mentioned above, phenacyl chlorides, for example, can be easily prepared by chlorinating a solution of acetophenone in glacial acetic acid. In one particularly advantageous procedure for carrying out the process according to the invention, acetophenone is therefore used as starting material and chlorinated with about 80% of the stoichiometrically required quantity of chlorine. Glacial acetic acid and unreacted acetophenone are removed by distillation at reduced pressure. The residue consists of practically pure phenacyl chloride and can be directly reacted with phenol without further treatment.

The new and very easily obtainable trisphenols, in particular tris-1,1,2-(o/p-hydroxyphenyl)-phenyl-ethanes, are well known to be suitable for the preparation of branched polycarbonates, which, in the molten state, have increased stability under load and pronounced non-Newtonian flow characteristics. Polycarbonates which have been branched with the new trisphenols therefore have important advantages over unbranched polycarbonates under processing conditions. In addition, polycarbonates which have been branched with the compounds according to the invention do not have the tendency to drip in when burning as have unbranched compounds.

The new trisphenols are also suitable for producing other materials such as epoxide resins and phenol formaldehyde resins, and after they have been reacted with a cyanogen halide they can also be used for the production of cyanate resins.

EXAMPLE 1

1,1,2-Tris-(o/p-hydroxyphenyl)-1-phenyl-ethane 1500 g of phenol and 232 g of phenacyl chloride are introduced into a reaction vessel and heated to 60° C. Hydrogen chloride is introduced until saturation point is reached and the mixture is slowly heated to between 80° and 85° C. It is then stirred at this temperature for 2 hours, during which time vigorous evolution of hydrogen chloride is observed. Hydrochloric acid and phenol are distilled off in a water jet vacuum and the hot residue is digested extracted twice with methylene chloride. 325 g of the crude product are recrystallised twice from a mixture of methanol and water with the addition of active charcoal, and the crystals are dried at 60° C. 268 g of colourless crystals melting at 262°-264° C are obtained. 92 g of unreacted phenacyl chloride can be isolated from the methylene chloride extracts by distillation at 91° – 95° C/3 Torr. This corresponds to a trisphenol yield of 77%, based on the degree of conversion.

$C_{26}H_{22}O_3$ (M.Wt 382.5). Calculated: C, 81.65; H, 5.80; 0,12.55; Phenol. OH, 13.33 %. Found: C, 81.4, H, 5.82; 0,12.8; Phenol. OH, 13.4 %.

Molecular weight: 370 (determined by vapour pressure osmometry in methanol at 37° C).

NMR ($d_6$ acetone/$d_6$ DMSO, TMS: $\tau = 10$): $\tau = 5.20$ ppm (—$CH_2$—), A,A', B,B' signal, centre of gravity $\tau = 3.14$ ppm, $J_{H,H}$ approx. 8 Hz.

If the reaction is carried out for 5 hours at 90° C only 48 g of unreacted phenacyl chloride can be isolated. The yield of recrystallised 1,1,2-tris-(p-hydroxyphenyl)-1-phenyl-ethane is 149 g. 254 g of a slowly crystallising solid is obtained. According to analyses and spectra, this is a mixture of o- and p-trisphenol.

EXAMPLE 2

1,1,2-Tris-(p-hydroxyphenyl)-1-phenyl-ethane
-Tris-(p-hydroxyphenyl)-

2.5 kg of acetophenone are dissolved in 9 kg of glacial acetic acid and the mixture is cooled to between 5° and 10° C. 1.15 kg of chlorine are introduced at this temperature. The reaction mixture is slowly heated when its colour has lightened, and the acetic acid is distilled off in a water jet vacuum. Towards the end of distillation, unreacted acetophenone is removed at 85° to 95° C/18 mm. The pale yellow residue contains 92 to 96% of phenacyl chloride.

10 kg of phenol are stirred into the crude phenacyl chloride at 40° to 45° C under a nitrogen atmosphere. The mixture is cooled to 30° C and 1.5 kg of concentrated $H_2SO_4$ are added dropwise. The temperature of the reaction mixture may be allowed to rise to about 35° C. It is stirred at this temperature for 12 hours. The reaction is slightly exothermic and can be recognised by the evolution of hydrogen chloride gas. The reaction mixture is heated to 40° C towards the end of the reaction and, as the evolution of hydrogen chloride gas slows down, the mixture is cooled and 1.4 kg of concentrated sodium hydroxide solution is added dropwise with vigorous cooling. After the addition of sodium hydroxide has been completed, the mixture is briefly heated to 90° C and then left to cool of its own accord. 15 l of methylene chloride are stirred in, followed by 5 l of water and the mixture is then suction filtered under nitrogen. The filter cake is suspended in boiling methylene chloride, filtered with vigorous suction and recrystallised twice from methanol/water with the addition of active charcoal and dried at 60° C.

Yield: 3.8 kg (63% of theoretical); Melting point: 260° C.

If concentrated phosphoric acid is used instead of sulphuric acid and a reaction temperature of 60° C is used, the yield of 1,1,2-tris-(p-hydroxyphenyl)-1-phenyl-ethane is 57%.

EXAMPLE 3

1,1,2-Tris-(p-hydroxyphenyl)-1-phenyl-ethane 150 ml of concentrated sulphuric acid are slowly added dropwise to 1 kg of phenol and 199 g of phenacyl bromide at 30° C and the reaction is then carried out as described in Example 2. 242 g (63.5% of theoretical) of trisphenol melting at 262° C are obtained.

EXAMPLE 4

1,1,2-Tris-(p-hydroxyphenyl)-1-p-methyl-phenyl-ethane 300 g of phenol are added to 50 g of ω-chloro-4-methylacetophenone (0.3 mol). 50 cc of concentrated sulphuric acid are added dropwise to this mixture at 32° – 35° C. The mixture is then stirred for 5 hours without special cooling means, poured on ice and taken up in methylene chloride. The extract is washed with water, aqueous sodium bicarbonate solution and again with water and dehydrated over sodium sulphate. It is then concentrated by evaporation in a water jet vacuum and the residue is digested several times with methylene chloride and recrystallised twice from a methanol/water mixture with the addition of active charcoal. 36 g of colourless crystals which melt at 247° to 251° C with decomposition are obtained. 25.8 g of unreacted of ω-chloro-4-methyl-acetophenone can be isolated from the combined methylene chloride phases by distillation at 85° C/0.1 mm. This corresponds to a conversion of 62%, based on trisphenol.

$C_{27}H_{24}O_3$ (M. Wt 396.5). Calculated: C, 81.79; H, 6.10; Phenol. OH, 12.86 %. Found: C, 81.5; H, 6.07; Phenol. OH, 12.9 %.

EXAMPLE 5

1,1,2-Tris-(p-hyroxyphenyl(-1-p-chlorophenyl-ethane

Hydrogen chloride gas is introduced to saturation point into a mixture of 76 g of 4 ω-dichloroacetophenone and 600 g of phenol at 60° C. The mixture is then heated to 80° C while the introduction of hydrogen chloride is continued. After 5 hours at 80° C, the reaction mixture is worked up by distilling off the phenol under vacuum and digesting the residue with methylene chloride. The product is recrystallised from methanol/water with the addition of active charcoal. 92 g of colourless crystals which melt at 268° to 269° C with decomposition are obtained. 19 g of unreacted 4,ω-dichloroacetophenone can be isolated from the combined methylene chloride phases. This corresponds to a conversion of 74%, based on the yield.

$C_{26}H_{21}ClO_3$ M. Wt 416.9). Calculated: C, 74.90; H, 5.08; Cl, 8.50; Phenol. OH, 12.26 %. Found: C, 74.6; H, 5.21; Cl, 8.69; Phenol. OH, 12.5 %.

Molecular weight: 406 vapour pressure osmometric determination in methanol).

EXAMPLE 6

1,1,2-Tris-(p-hydroxyphenyl)-1-p-nitrophenyl-ethane 45 cc of concentrated sulphuric acid are introduced dropwise into a mixture of 70 g of ω-chloro-4-nitroacetophenone and 300 g of phenol at 30° to 40° C. The procedure is then continued as described in Example 2. 59 g of pale yellow crystals having a decomposition point of 264°–266° C are obtained and 31 g of unreacted ω-chloro-4-nitroacetophenone can be isolated by distillation at 124°–126° C/0.02 mm. This corresponds to a conversion of 69% based on the yield.

$C_{26}H_{21}NO_5$ M. Wt 427.5). Calculated: C, 73.06; H, 4.95; N, 3.27; Phenol. OH, 11.93 %. Found: C, 72.7; H, 5.08; N, 3.44; Phenol. OH, 11.8 %.

EXAMPLE 7

1,1,2-Tris-(4-hydroxy-2-methyl-phenyl)-1-phenyl-ethane

Gaseous hydrogen chloride is introduced into a mixture of 154.6 g of phenacyl chloride and 1000 g of o-cresol at 50° C until saturation point is reached. The mixture is then heated while the introduction of hydrogen chloride is continued and after 5 hours reaction at 90° to 100° C the mixture is distilled under vacuum. The residue is digested with cold toluene and recrystallised from toluene. 296 g of colourless crystals melting at 216°–226° C are obtained. 24 g of unreacted chloroacetophenone can be isolated from the toluene phase after digestion. This corresponds to a trisphenol yield of 83%, based on the degree of conversion.

$C_{29}H_{28}O_3$ M. Wt 424.5). Calculated: C, 82.04; H, 6.65; Phenol. OH, 12.01 %. Found: C, 81.6; H, 6.42; Phenol. OH, 12.2 %.

Molecular weight: 398 (vapour pressure osmometric determination in methanol).

EXAMPLE 8 (Application)

2.97 ((30 mol) of phosgene are introduced with stirring at 20° to 25° C in the course of 135 minutes into a mixture of 4.566 kg of bis-2-(4-hydroxyphenyl)-propane (20 mol), 15.3 g (0.04 mol ≙ 0.2 mol %) of 1,1,2-tris-p-hydroxyphenyl)-1-phenylethane, obtained according to Example 7, 75.1 g (0.5 mol) of p-tert.-butylphenol (2.5 mol %), 3,65 kg (approx. 41 mol) of 45 % sodium hydroxide solution, 32 l of distilled water and 35 l of methylene chloride. 27.7 ml of triethylamine (1 mol %) are then added.

After the mixture has been stirred for a further hour, the organic phase is separated, washed several times with 2 % sodium hydroxide solution, 2 % phosphoric acid and distilled water and finally worked up by the addition of chlorobenzene and distillation to remove methylene chloride. The solution in chlorobenzene gels on cooling and is then dried at 80° C/15 Torr for 15 hours, granulated and again dried at 120° C/15 Torr for 48 hours.

The relative viscosity of the resulting product is $\eta_{rel} = 1,404$ (determined at 25° C in $CH_2Cl_2$, 5 g/1000 ml solution).

The average molecular weight determined by the light scattering method is $\overline{M}_{LS} = 51,300$ ($M\eta = 42,800$). The branched structure and hence incorporation of the branching agent is quite clearly recognizable from the difference between the molecular weight determinations. The properties of the polycarbonate are set forth in Table 1.

EXAMPLE 9

The procedure is the same as in Example 8 but using 90 g (3.0 mol %) of p-tert.-butylphenol. $\eta_{rel} = 1.337$, $\overline{M}_{LS} = 38,500$, $M\eta = 35,300$. The properties of the polycarbonate are set forth in Table 1.

Table 1

| Table of properties | Product according to Example 8 | Product according to Example 9 | Unbranched polycarbonate |
|---|---|---|---|
| ηrel | 1.404 | 1.337 | 1.34 |
| Standardized notched impact strength (KJ/m²) DIN 53 453 | 49.5 | 50.6 | 49.5 |
| Impact strength (KJ/m²) DIN 53 453 | unbroken | unbroken | unbroken |
| Arborg test *) (mm) | 182 | 189 | torn off |
| O₂ Index **) (%) | 33 | 33 | 25 |

Apparent melt viscosity in dependence upon the velocity of deformation ***)

| | Product according to Example 9 | | | | Unbranched polycarbon | |
|---|---|---|---|---|---|---|
| Apparent melting point viscosity η_m [Pa.s] | 5.10³ | 2.8.10³ | 7.5.10² | 1.3.10³ | 1.25.10³ | 1.10³ |
| Velocity of deformation [secs⁻¹] | 10¹ | 10² | 10³ | 10¹ | 10² | 10³ |

*) In the Arborg test, the molten material is forced out of a piston which is open at the bottom, through an annular nozzle of standard dimensions in 5 strokes at a constant temperature of 250° C. The deformation of the material extruded by strokes 2 – 4 is measured and indicated in mm. Unbranched polycarbonate drips off very rapidly so that a measurement cannot generally be obtained.
**) ASTM-D-2863-70, the larger the number, the better are the properties of the product
***) Length of nozzle: φ 3 20, Temperature 300° C

We claim:
1. Trisphenols [1,1,2-tris-(o/p-hydroxyphenyl)-1-phenylethanes] of the general formula (I):

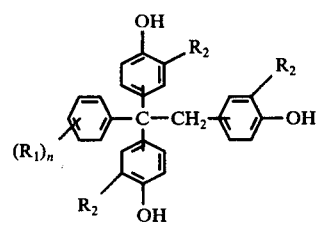

(I)

wherein $R_1$ and $R_2$, which may be the same or different, denote hydrogen, a $C_1$–$C_{18}$ alkyl group, a cyclohexyl group or an optionally substituted $C_6$–$C_{15}$ aryl group, a halogen or a nitro group, and n represents an integer from 1 to 5.

2. The trisphenols of claim 1 wherein said optionally substituted $C_6$–$C_{15}$ aryl group is phenyl.

3. The trisphenols of claim 1 wherein $R_1$ is hydrogen and n is 1.

4. The trisphenol of claim 3 wherein $R_2$ is hydrogen.

* * * * *